United States Patent [19]

Salter et al.

[11] 3,933,926

[45] Jan. 20, 1976

[54] PREPARATION OF NITROPHENOLS

[76] Inventors: David Anthony Salter, 35, Roseacres, Takely, Essex, England; Robert John James Simkins, 3, Upper Park, Harlow, Essex, England

[22] Filed: May 30, 1973

[21] Appl. No.: 365,208

Related U.S. Application Data

[63] Continuation of Ser. No. 880,981, Nov. 28, 1969, abandoned.

[30] Foreign Application Priority Data

Nov. 29, 1968 United Kingdom............ 56724/68
Aug. 27, 1969 United Kingdom............ 42571/69

[52] U.S. Cl. ..................... 260/622 P; 260/621 N
[51] Int. Cl.$^2$................ C07C 79/26; C07C 79/30
[58] Field of Search ........ 260/622 R, 622 P, 621 N; 880/981

[56] References Cited
UNITED STATES PATENTS
2,301,912  11/1942  Jones et al. ................... 260/622 R

*Primary Examiner*—James O. Thomas, Jr.
*Assistant Examiner*—W. B. Lone
*Attorney, Agent, or Firm*—Stevens, Davis, Miller & Mosher

[57] ABSTRACT

A process for the preparation of nitrophenols by adding over a period of time a suspension containing from about 4 to about 20 per cent weight/volume of nitrosated phenol to a nitric acid solution containing between 45 and 100 per cent by weight of nitric acid, said solution being maintained at a temperature in the range from about 45° to 100°C.

10 Claims, No Drawings

PREPARATION OF NITROPHENOLS

This application is a continuation of Ser. No. 880,981 filed Nov. 28, 1969, now abandoned.

The invention relates to improvements in or relating to processes for the preparation of nitrophenols.

The direct nitration of phenols to produce mono- and polynitro derivatives is a highly exothermic and vigorous reaction which can be controlled only with great difficulty. As a consequence, this operation is hazardous and, in addition, the purity of the product may be variable. It has, therefore, been found necessary in the preparation of nitrophenols to avoid the direct nitration of the phenol and to employ processes which initially form an intermediate compound which may then be nitrated. Phenol, for instance, is first sulphonated to form a mixture of phenolsulphonic acids which are then nitrated to produce picric acid (2, 4, 6strinitrophenol). Resorcinol is treated similarly to give styphnic acid, and phloroglucinol is firstly converted to a triacetoxy derivative which is nitrated to produce trinitrophloroglucinol. These additional steps in the process are both time-consuming and costly as they involve the preparation and separation of intermediate compounds and sometimes introduce other difficulties associated with the use of mixed mineral acids.

Another method of preparing nitro-phenols is by hydrolysis of an appropriate halogeno derivative. Thus 2,4-dinitrochlorbenzene is hydrolysed by aqueous alkali to give, 2,4-dinitrophenol, which may be subsequently nitrated to picric acid. Similarly, tribromotrinitro-benzene may be hydrolysed to give trinitrophloroglucinol. These processes do not offer significant savings in time and labour, and the action of the alkali on the nitro groups may be such as to introduce unwanted decomposition products thus giving impure products.

It has now been found that nitrophenols may be prepared in a cheap and convenient way in a high state of purity, uncontaminated with sulphate or chloride anions, by passing a suspension or slurry of the nitroso derivative of the phenol into nitric acid to provide the required nitrophenol.

According to the invention, there is provided a process for the preparation of nitrophenols comprising, adding over a period of time, a liquid suspension containing from about 4 to about 20 percent weight/volume of the nitrosated phenol to a nitric acid solution containing between 45 and 100 percent by weight of nitric acid, said solution being maintained at a temperature in the range from about 45° to 100°C preferably between 45° and 75°C.

The oxidation of the nitrosophenol is finally completed by maintaining the reactants at a temperature normally between about 80° and 100°C for a sufficient time normally 1 to 3 hours to ensure the complete conversion of the nitrosophneol to the required nitro compound.

For the preparation of styphnic acid, it has been found that a liquid suspension containing about 5 to about 15 percent weight/volume of the nitroso resorcinol may be used and a preferred temperature range of the nitric acid solution is between about 55° to 60°C.

Nitrosophenols which may be nitrated by the process of the invention may be derived from mono- and polyhydric phenols with a single or multi-ring nucleus. The hydrogen atoms of the nucleus may be substituted in positions other than those in which it is desired to insert a nitro-group. Such substituents include alkyl groups, ether groups or a group capable of polymerising to produce a polymeric compound.

The nitrosophenol for use in the process of the invention may contain one or more nitroso groups. Thus, for instance, mono-nitroso phenol may be used as the starting material for mono-nitrophenol or dinitrophenol - the final product being dependent on the reaction conditions — and 2,4-dinitrosoresorcinol may be used in the preparation of styphnic acid (2,4,6-trinitroresorcinol).

The process of the invention is particularly suitable for the preparation of the trinitro derivatives of phenol, resorcinol, phloroglucinol, anisole and phenetole from mono-nitrosophenol, dinitrosoresorcinol, trinitrosophloroglucinol, mono-nitroso anisole and mono-nitrosophenetole respectively.

The term liquid suspension in the specification includes suspensions in water and in mineral acids diluted with water and the proportion in the suspension or slurry quoted as percentage weight/volume is defined as the number of grammes of solid in 100 ml. of liquid.

It will be appreciated that the temperature and concentration of the acid and the concentration of the suspension or slurry are inter-related. Thus, for instance, the temperature of the acid may be at the lower end of the range when the acid concentration is relatively high and especially when the slurry concentration is also relatively high. It is essential, however, that the critical temperature of the acid and hence the reaction temperature is sufficiently high to ensure that the reaction takes place soon after the admixture of the reactants without an induction period to avoid a violent uncontrolled reaction. The temperature of the acid bath may be controlled by any known means such as an external bath and/or variations in the rate of addition of the slurry. The dilution of nitric acid solution by water, especially those solutions containing 70 or more percent by weight of nitric acid is accompanied by an evolution of heat and the addition of the nitrosophenol slurries into such solutions should be made slowly to avoid an uncontrollable rise in temperature.

It has been found that the nitroso derivatives may be more easily oxidised when there are a plurality of hydroxyl groups on the phenol nucleus. Thus, the nitroso derivatives of phloroglucinol are conveniently converted to trinitrophloroglucinol by the action of 65 percent nitric acid over 30 minutes at 50°C whereas dinitrosophenol requires stronger acid over a period of several hours at 90°C to effect complete conversion to picric acid.

Intermediate nitrophenols such as mono- and dinitrophenols, for instance dinitroresorcinol and dinitrophenol, may be prepared by the process of the invention by variation of one or more of the reaction conditions of acid concentration, temperature and time. In particular, the lower reactivity of the monohydric phenols permits the isolation of such intermediates, for instance, 2,4-dinitrophenol, in a high state of purity.

Whereas, it is normally more convenient to add the nitrosophenol slurry to the acid bath in conditions of maximum temperature and acid concentration to give, with safety, the minimum reaction time, the process of the invention may be adapted in certain circumstances to allow the nitrosophenol slurry to be passed into nitric acid of low acid strength and at a low temperature to effect a partial nitration of the phenol. This partially nitrated product may then be separated from the mother liquor by filtration or any other means and subsequently further nitrated using highly concentrated acid at a higher temperature. For instance, 2,4-dinitrophenol produced by such a nitrosation/oxidation process is in the form of small spherical granules. These granules are particularly suitable for decantation of filtration and, in addition, markedly reduce the danger of inhalation of toxic dust thus reducing the health hazard which is normally present in the manufacture of this material.

In one aspect of the invention, the phenol is nitrosated by known means as for instance a mixture of acid and sodium nitrite and the resultant slurry of the nitroso-compound is passed into a nitration/oxidation bath of the required concentration and temperature. The proportions of the initial reactants may be so chosen to ensure that the suspension contains from about 4 to about 20 percent of the nitrosophenol. Using this method, 1 mole styphnic acid has been prepared from resorcinol in 85 percent yield in four hours in a simple plant as the solution contains only one mineral acid and not a mixture of at least two.

By comparison a similar yield by the sulphonation/nitration process required ten hours and, as sulphuric acid was also present, there were also problems associated with the use of mixed mineral acids.

Alternatively, the aqueous suspension may be reduced in volume by filtration, decantation or any other known means.

Similarly, this method has been used successfully to prepare picric acid and trinitrophloroglucinol from phenol and phloroglucinol respectively. It is well known that there are distinctive differences in the rate of nitrosation of phenols. It is therefore possible by the limitation of the amount of nitrosating agent to prepare mono-, di- or tri-nitrose compounds. Thus by the careful selection of the nitroso compound and the reaction condition of acid concentration and temperature; it is possible to prepare mono- or other nitrophenols.

Phenols for use in this aspect of the invention may be added to the solution as such or when the phenol to be used in relatively insoluble in aqueous solutions, e.g. phenol itself or phloroglucinol, it may be added as a salt, preferably the sodium or potassium salt.

In another aspect of the invention, there is provided a process for the preparation of nitrophenols wherein the phenol is firstly sulphonated, then nitrosating the sulphonated product and passing the resultant slurry into nitric acid of the required concentration. For instance, resorcinol may be firstly sulphonated and then nitrosated to give 2,4-dinitrosoresorcinol. The latter compound may then be passed as a slurry into nitric acid to give styphnic acid.

The nitrophenols made by the process of the invention may be used as explosives or propellants or may be used in the preparation of dye stuffs.

The invention is illustrated by the following examples:-

EXAMPLE 1

47 gm. phenol was dissolved at room temperature in a solution of 21 gm. sodium hydroxide and 43 gm. sodium nitrite in 500 ml water with stirring in a suitable flask. 500 gm. crushed ice was added, and then 400 ml of nitric acid (26 percent w/v) added slowly at a rate such that the temperature remained below 40°C. The addition took about 20 minutes. The solution was held at about 5°C for 30 minutes, and then the resultant slurry of nitrosophenol (4.4 percent w/v) was pumped in to a reaction vessel containing 200 ml of hot nitric acid (60 percent w/v). The temperature of the oxidizing mixture was kept at 60°–70°C by sparging steam into an external bath, and by adjusting the rate of the addition to the cold slurry. The addition took about 15 minutes. During the first part of the addition there was a moderate evolution of nitrous fumes, and these were removed by passing a stream of air through the vessel. The mixture was held at 90°C for 1.5 hours, then cooled to ambient temperature and the 2,4-dinitrophenol filtered, washed with water, and dried m.p. 113.5°C. Yield 79 percent.

EXAMPLE 2

47 gm. phenol was dissolved at room temperature in a solution of 21 gm sodium hydroxide and 43 gm sodium nitrite in 100 ml of water, and the resultant solution added slowly to a mixture of 150 ml nitric acid (70 percent w/v) and 400 gm crushed ice, while keeping the temperature below 5°C. The addition took about 40 minutes. The mixture was held at 15°C for 30 minutes and then treated with 200 ml nitric acid (70 percent w/v). The mixture was held at 65°C for 1 hour and at 91°C for 2 hours, then cooled and the 2,4-dinitrophenol filtered, washed with water, and dried. Yield 70 percent.

EXAMPLE 3

The conditions and quantities used were identical with those of Example 1, except that 21.5 gm of sodium nitrite were used. The yield of 2,4-dinitrophenol was 71 percent.

EXAMPLE 4

The conditions and quantities used were identical with those of Example 1, except that 86 gm of sodium nitrite were used. The yield of 2,4-dinitrophenol was 74 percent.

EXAMPLE 5

47 gm. phenol was dissolved at room temperature in a solution of 21 gm. sodium hydroxide and 43 gm. sodium nitrite in 500 ml water in a suitable flask. 400 ml nitric acid (26 percent w/v) were added slowly, using external cooling to keep the temperature below 0°C. The solution was held at about 5°C for 30 minutes and the resultant slurry of nitrosophenol (6.9 percent w/v) was pumped into a vessel containing 1 litre of hot fuming nitric aicd (d 1.49). The temperature was held at 50°–60°C by alternate use of external heating and cooling and by adjustment of the rate of addition. The mixture was heated at 96°C for 3 hours, then cooled, and the picric acid filtered, washed with water, and dried, m.p. 121°C. Yield 65 percent.

EXAMPLE 6

The conditions and quantities used were identical with those of Example 1, except that after filtration the 2,4-dinitrophenol was added to 200 ml of nitric acid (84 percent w/v) and heated at 95°C for 3 hours before being cooled and filtered to give pure picric acid, m.p. 123.1°C. Yield 60 percent.

EXAMPLE 7

The conditions and quantities used were identical with those of Example 6, except that 350 ml of nitric acid (60 percent w/v) were used for the second stage.

Yield of picric acid 76.5 percent, m.p. 123.0°C.

EXAMPLE 8

92 gm of crude picric acid, m.p. 113.2°C was dissolved in 100 ml of fuming nitric acid (d 1.49) at room temperature. The solution was held at 20°C for 10 minutes, and then diluted slowly with 100 ml ice-water to precipitate pure poric acid, m.p. 123.1°C, recovery 89 percent.

EXAMPLE 9

The conditions and quantities used were identical with those of Example 6, except that 150 ml of recrystallization liquor (of. Example 8) were used for the second stage. Yield of picric acid 93.0 percent, m.p. 117.3°C; after recrystallization m.p. 122.3°C, recovery 86 percent.

EXAMPLE 10

The conditions and quantities used were identical with those of Example 6, except that a solution of recrystallization liquor in water was used for the first stage. Yield of picric acid 79.1 percent, m.p. 105.8°C; after recrystallization m.p. 122.8°C, recovery 87 percent.

EXAMPLE 11

The conditions and quantities were identical with those of Example 1, except that the oxidation was made with 300 ml of nitric acid (60 percent w/v) over 3 hours at 95°C. The product was a mixture of 2,4-dinitrophenol and picric acid, m.p. 80°C.

EXAMPLE 12

10.8 gm m-Cresol was dissolved at room temperature in a solution of 7.5 gm sodium nitrite and 4.0 gm sodium hydroxide in 20 ml water, and added dropwise to a mixture of 10 ml fuming nitric acid and 50 gm crushed ice, keeping the temperature below 0°C. The mixture was held at 5°C for 15 minutes, and then as a 10.5 percent w/v slurry pumped into 50 ml of hot nitric acid (60 percent w/v). The mixture was held at 95°C for 1.5 hours, then cooled to ambient temperature, and the methylpicric acid filtered, washed with water, and dried. Yield 55 percent.

EXAMPLE 13

22 Kgm of resorcinol, 84 litres of nitric acid (16.5 percent w/v) and 190 Kgm of crushed ice were placed in a suitable stainless steel vessel fitted with a stirrer. When the resorcinol had dissolved, a solution of 30 Kgm sodium nitrite in 183 litres of water was added over 35 minutes, vigorous stirring being used to prevent local overheating. The resultant ice-cold slurry of dinitrosorescorcinol monohydrate (8.2 percent w/v) was pumped into 80 litres of hot nitric acid (60 percent w/v) over 2 hours, while the temperature was maintained at 60 ± 5°C and adequate stirring was used. The reaction mixture was then heated to 82°C over 15 minutes and stirred for a further 45 minutes while the temperature was slowly raised to 97°C. The mixture was then cooled to 15°C over 5 minutes and the styphnic acid filtered off, washed with water and dried. Yield 46 Kgm (94 percent),

EXAMPLE 14

The conditions and quantities were identical to those used in Example 13, except 300 Kgm crushed ice were added, to give a slurry of 6.4 percent w/v. The yeidlwas 87.2 percent.

EXAMPLE 15

110 gm resorcinol were dissolved at room teperature in 68 ml of fuming nitric acid and 1,650 ml water with stirring in a suitable flask. 2,000 gm crushed ice were added and then a solution of 150 gm sodium nitrite in 370 ml water was added at such a rate that the temperature of the vigorously stirred mixture remained between 0° and 5°C. The addition took about 20 minutes. Ice in an external bath was used for temperature control. The reactants were held at about 5°C for 30 minutes and 2750 ml of nitrosation liquor were filtered off — filtration being easy. The remaining slurry of dinitrosoresorcinol monohydrate (14.1 percent w/v) was pumped into a reaction vessel containing 370 ml of nitric acid (60 percent w/v) held at a temperature of 55°–60°C. The addition took about 30 minutes. After the addition, the mixture was held at a temperature of 60°C for a further 30 minutes and then heated to 95°C over 45 minutes. The mixture was cooled to ambient temperature, and the styphnic acid was filtered, water washed and dried. Yield 85 percent.

EXAMPLE 16

110 gm resorcinol were dissolved at room temperature in a solution of 68 ml of fuming nitric acid (d 1.50) in 325 ml water in a three litre flask. 1,500 gm crushed ice were added and then a solution of 150 gm of sodium nitrite in 370 ml water at such a rate that the temperature of the vigorously stirred mixture remained between 0° and 5°C. The addition took about 30 minutes. The mixture was held at about 5°C for 30 minutes and then the resultant slurry of dinitrosoresorcinol monohydrate (8.3 percent w/v) was pumped into a reaction vessel containing 400 ml nitric acid (60 percent w/v). The temperature of the oxidizing mixture was kept at 55°–60°C by sparging steam into an external bath and by adjusting the rate of the addition of the cold slurry. The addition took about 30 minutes. Copious nitrous fumes were evolved during the first part of the addition and these were removed by a stream of air passing through the flask. The mixture was held at 60°C for a further 30 minutes and then heated to 95°C over a period of 45 minutes. The mixture was then cooled to ambient temperature, filtered and the styphnic acid washed with water and dried. Yield 90 percent.

EXAMPLE 17

16.2 gm of phloroglucinol was dissolved at 30°C in a solution of 27.6 gm sodium nitrite and 8.0 gm sodium hydroxide in 25 ml water, and added slowly to a mixture of 21 ml fuming nitric acid (d 1.51) and 108 gm crushed ice, vigorous stirring being used to ensure that the temperature remained below 5°C. The mixture was held at 15°C for 20 minutes, and then pumped as a 14.6 percent w/v slurry into 100 ml of hot nitric acid (65 percent w/v) at 50°C. The mixture was cooled to 0°C and trinitrophloroglucinol filtered, washed with a little water, and dried. Yield 73 percent.

EXAMPLE 18

A solution of 690 ml nitric acid (70 percent w/v) in 750 ml ice-water was slowly pumped into a vigorously stirred solution of 324 gm phloroglucinol, 160 gm sodium hydroxide and 455 gm sodium nitrite in 1500 ml water. The temperature was maintained at 0°–5°C by an external cooling bath. The resultant slurry (17.6 percent w/v) of trinitrosophloroglucinol was held at 15°C for 15 minutes, then pumped into 2,000 ml nitric acid (65 percent w/v) while keeping the temperature at 50°C. The mixture was held at 50°C for 45 minutes then cooled to 10°C and the trinitrophloroglucinol filtered and washed with a little water. Yield 78.2 percent.

EXAMPLE 19

The conditions and quantities used were identical with those of Example 18, except that 2500 ml of nitric acid (65 percent w/v) was used for oxidation, and the oxidation temperature was 45°C. Yield 74 percent.

EXAMPLE 20

A solution of 130 ml nitric acid (70 percent w/v) in 200 ml ice-water was added slowly to a vigorously stirred solution of 75 gm 3-tertbutylphenol, 20 gm sodium hydroxide and 37 gm sodium nitrite in 250 ml water. The temperature was maintained at 0°–5°C by an external cooling bath. The mixture was held at 10°C for 30 minutes, then heated at 100°C for 1 hour to produce a suspension of a red-brown tar in an aqueous medium. The mixture was cooled, the aqueous phase decanted and replaced with 210 ml of nitric acid (50 percent w/v). This mixture was stirred at 100°C for three hours then cooled to precipitate tertbutylpicric acid. Yield 70 percent.

EXAMPLE 21

A solution of 26 ml nitric acid (70 percent w/v) in 50 ml ice-water was added slowly to a solution of 12.6 gm 3-ethyl-5-methylphenol, 4 gm sodium hydroxide and 7.6 gm sodium nitrite in 75 ml water. The temperature was maintained at 0°–5°C by an external cooling bath. The resultant mixture was held at 10°C for 10 minutes, then heated at 100°C for 90 minutes before being allowed to cool overnight. The aqueous phase was then decanted from the oil present, and replaced with 80 ml nitric acid (60 percent w/v). The mixture was stirred at 65°C for 1 hour, then cooled to precipitate crude ethylmethylpicric acid, which was purified by recrystallization from petroleum ether. Yield 45 percent.

EXAMPLE 22

A solution of 12.6 ml nitric acid (70 percent w/v) in 100 ml water was added slowly to a solution of 12.2 gm 3,5-dimethylphenol, 4 gm sodium hydroxide and 7 gm sodium nitrite in 150 ml water. The temperature was maintained at 0°–5°C by an external cooling bath. The mixture was held at 5°C for 2.5 hours, and then concentrated by filtration. The resultant slurry (15 percent w/v) was added slowly to 100 ml nitric acid (45 percent w/v) at 80°C with vigorous stirring. The mixture was held at 80°C for 45 minutes then cooled and filtered to give dimethyl-picric acid. Yield 72 percent.

EXAMPLE 23

A solution of 13 ml nitric acid (70 percent w/v) in 35 ml water was added slowly to a solution of 11.2 gm 3-methoxyphenol, 4 gm sodium hydroxide and 7.5 gm sodium nitrite in 60 ml water, using vigorous stirring. The temperature was maintained at 0°–5°C by an external cooling bath. The resultant mixture (13.4 percent w/v slurry) was held at 10°C for 10 minutes, then pumped into 125 ml nitric acid (65 percent w/v) at 50°C. The mixture was stirred at 85°C for 30 minutes, then cooled to precipitate 4,6-dinitro-3-methoxyphenol as pink crystals, m.p. 110°C. The mother liquor was decanted and the crystals added to hot nitric acid (98 percent w/v) on a steam bath; after 10 minutes the solution was drowned to precipitate methyoxypicric acid, m.p. 85°C. Yield 64 percent.

EXAMPLE 24

A solution of 72 gm 1-naphthol, 20 gm hydroxide and 38 gm sodium nitrite in 250 ml water was added slowly to a well stirred solution of 70 ml nitric acid (70 percent w/v) in 200 ml water. The mixture was maintained at 0°–5°C by an external cooling bath. The mixture (8.1 percent w/v slurry) was held at 10°C for 30 minutes, then pumped into a solution of 200 ml nitric acid (70 percent w/v) in 200 ml water at 45°C. The mixture was held at 50°C for 1.5 hours then cooled to precipitate a mixture of 2-nitro-1-naphthol and 2,4-dinitro-1-naphthol, which was separated by chromatography.

What we claim is:

1. A process for the preparation of polynitrophenols comprising adding over a period of time sufficient to form said polynitrophenols, a liquid suspension containing from about 4 to about 20 percent weight/volume of a nitrosated phenol selected from the group consisting of nitrosated phenol, nitrosated m-cresol, nitrosated resorcinol, nitrosated phloroglucinol, nitrosated 3,5,dimethyl phenol, nitrosated 3-methoxy phenol and nitrosated naphthol to a nitric acid solution containing between 45 and 100 percent by weight of nitric acid, said solution being maintained at a temperature in the range from about 45° to 100°C., said nitrosated compound containing at least one nitroso group, said polynitrophenol containing at least the same number of nitro groups as nitroso groups on said nitrosated compound.

2. The process according to claim 1, wherein the temperature of the reactants is subsequently raised to and maintained at a temperature between about 80° and about 100°C. for a sufficient time whereby the complete conversion of the nitrosophenol to the nitrophenol is ensured.

3. The process according to claim 1, wherein the phenol is selected from the group consisting of phenol, resorcinol and phloroglucinol.

4. The process according to claim 1, wherein the phenol is added to the initial reactants as a soluble salt.

5. The process according to claim 4, wherein the soluble salt is selected from the group consisting of sodium and potassium salts.

6. A process for the preparation of styphnic acid comprising adding a liquid suspension containing from about 4 to about 20 percent weight/volume of 2,4-dinitroso resorcinol over a period of time sufficient to form styphnic acid to a nitric acid solution containing between 45 and 100 percent by weight of nitric acid, said solution being maintained at a temperature in the range from about 45° to 100°C.

7. The process according to claim 6, wherein the liquid suspension contains from about 5 to about 15 percent weight/volume of dinitroso resorcinol and the nitric acid solution is maintained at a temperature in the range from about 45° to about 75°C.

8. The process according to claim 7, wherein the nitric acid solution is maintained at a temperature in the range from about 55° to about 60°C.

9. A process for the production of picric acid comprising adding a liquid suspension containing from about 4 to about 20 percent weight/volume of mono-nitroso phenol over a period of time sufficient to form picric acid to a nitric acid solution containing between 45 and 100 percent by weight of nitric acid, said solution being maintained at a temperature in the range from about 45° to 100°C.

10. A process for the production of trinitrophloroglucinol comprising adding a liquid suspension containing from about 4 to about 20 percent weight/volume of trinitrosophloroglucinol over a period of time sufficient to form trinitrophloroglucinol to a nitric acid solution containing between 45 and 100 percent by weight of nitric acid, said solution being maintained at a temperature in the range from about 45° to 100°C.

* * * * *